United States Patent [19]

Hough et al.

[11] Patent Number: 5,739,139
[45] Date of Patent: Apr. 14, 1998

[54] ACETAMINOPHEN AND DIMENHYDRINATE ANALGESICS

[75] Inventors: Douglas R. Hough, Morrisville; Edward B. Nelson, Lower Gwynedd; Robert B. Raffa, Norristown, all of Pa.

[73] Assignee: McNeil-PPC, Inc., Skillman, N.J.

[21] Appl. No.: 667,054

[22] Filed: Jun. 20, 1996

[51] Int. Cl.⁶ .......................... A61K 31/52; A61K 31/165
[52] U.S. Cl. .......................................... 514/263; 514/264
[58] Field of Search ........................................ 514/263, 264

[56] References Cited

U.S. PATENT DOCUMENTS

| | | | |
|---|---|---|---|
| 2,499,058 | 2/1950 | Cusic | 514/263 |
| 4,466,960 | 8/1984 | Silverman et al. | 514/263 |
| 4,567,183 | 1/1986 | Sunshine et al. | 514/264 |
| 4,656,177 | 4/1987 | Sunshine et al. | |

OTHER PUBLICATIONS

The Merck Index, 10ᵗʰ Edn., pp. 225–226, 467, 1327 (1983).

*Primary Examiner*—James H. Reamer

[57] ABSTRACT

Disclosed are compositions comprising acetaminophen (APAP) and dimenhydrinate and methods for their use in analgesia. When acetaminophen and dimenhydrinate are within certain ratios, their pharmacological effects are super-additive.

13 Claims, 1 Drawing Sheet

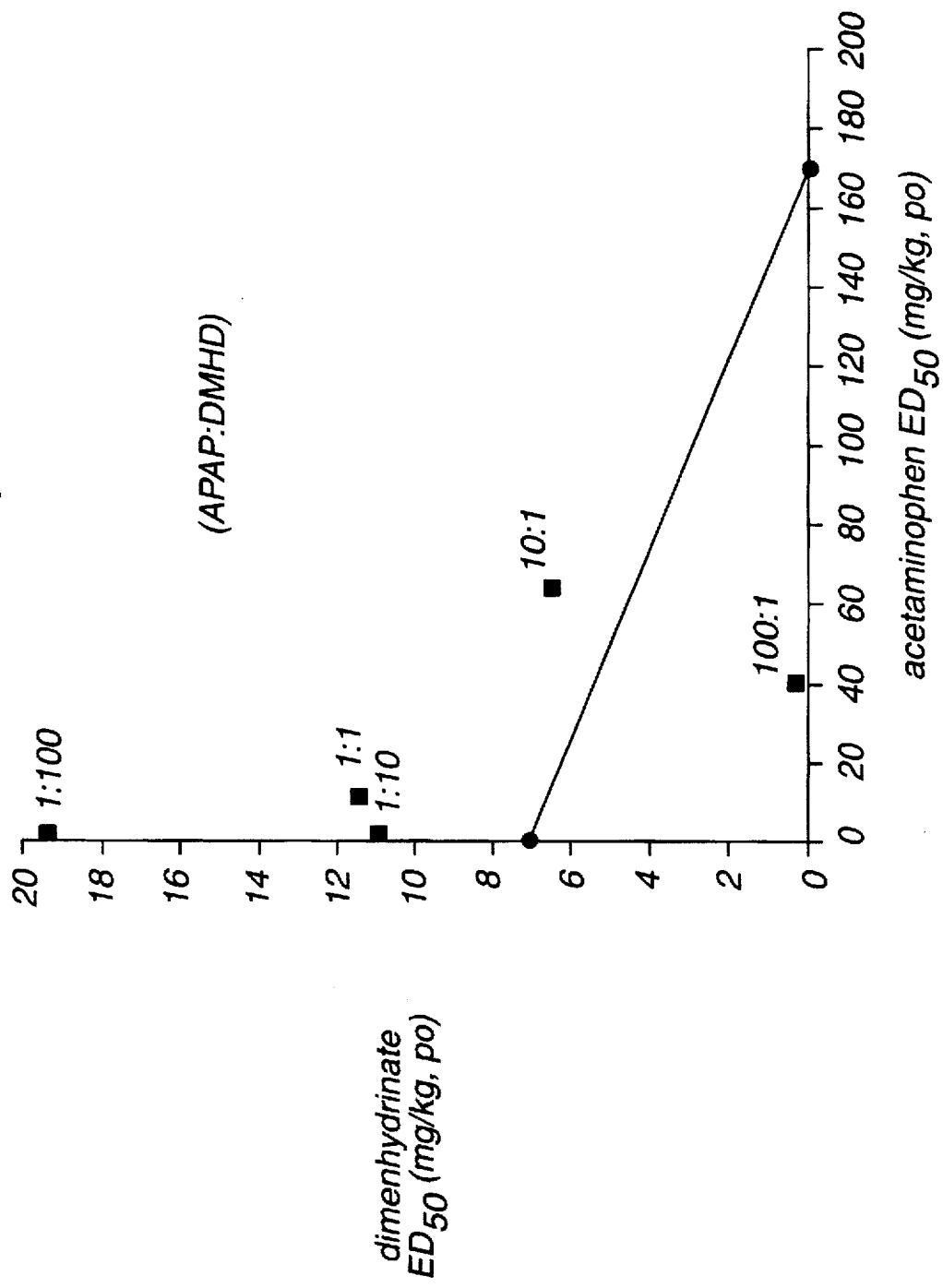

ACETAMINOPHEN AND DIMENHYDRINATE ANALGESICS

The present invention relates to analgesic compositions. More particularly, the present invention relates to analgesic compositions containing acetaminophen and dimenhydrinate.

BACKGROUND OF THE INVENTION

Acetaminophen, N-(4-hydroxyphenyl)acetamide or herein referred to as APAP, was first used in medicine by Van Mering in 1893, but only since 1949 has it gained in popularity as an effective alternative to aspirin for

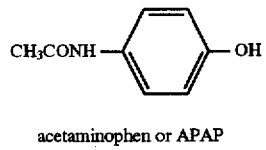

acetaminophen or APAP analgesic uses in the over the counter market. The pharmacology of APAP is reviewed by B. Ameer et al., Ann. Int. Med., 87, 202 (1977), and the preparation of APAP is disclosed in U.S. Pat. No. 2,998,450. Considering the widespread use of APAP and the volume of its manufacture, both its manufacture and its use as an analgesic is well known to persons skilled in the art.

Research for improved analgesics has split into two branches. In the more traditional branch, research continues for new analgesic compounds. Recent years have seen the introduction of a number analgesic products having active ingredients not previously available. In the second branch, research has been considerably increased in the area of combination products. In combination products, improvement in analgesic effect is looked for in the interaction between two or more coadministered active ingredients. With the risk and expense associated with introducing new active compounds to the market, improved safety and efficacy in analgesic products might be better obtained by using combinations of known active compounds.

Considering the advantages of working with APAP and its widely accepted use, it is of particular interest to persons investigating the advantages of combination products. It is known in the prior art to formulate so-called "nighttime analgesics", consisting of an aspirin layer and an APAP layer; the latter also containing the sleep-aid methapyrilene fumarate. A tablet of this type is described in the "Physicians Desk Reference", 28th ed., 1974, page 640 (published by Medical Economics Company, Oradell, N.J.). A. Pircio et al., Arch. Int. Pharmacodyn., 235, 116 (1978) report superadditive analgesia with a 1:125 mixture of butorphanol, an opioid analgesic, and APAP, whereas a 1:10 mixture did not show a statistically significant superadditive effect. G. Stracher et al., Int. J. Clin. Pharmacol. Biopharmacy, 17, 250 (1979) report that the combination of the non-opioid analgesics, tolmetin and APAP, allows for a marked reduction in the amount of tolmetin required to produce analgesia. U.S. Pat. No. 4,260,629 discloses that an orally administered composition of APAP and zomepirac, a non-opioid analgesic, in a particular weight ratio range produces a superadditive relief of pain in mammals. Furthermore, U.S. Pat. No. 4,132,788 discloses that 5-aroyl-1-(lower) alkylpyrrole-2-acetic acid derivatives, non-opioid analgesics, when combined with APAP or aspirin exhibit superadditive antiarthritic activity. Also, U.S. Pat. No. 5,336,691 discloses that the combination of tramadol, a centrally active analgesic, and APAP exhibits a synergistic analgesic effect when combined in certain ratios. G. B. Pat. No. 1,442,159 teaches that combinations of APAP and diphenhydramine hydrochloride in certain proportions are satisfactory in the treatment of migraine headache. U.S. Pat. Nos. 4,401,665 and 4,505,862 disclose combinations of aspirin, APAP and diphenhydramine dihydrogencitrate for use as an analgesic.

It is an object of the present invention to combine APAP with a second active ingredient to produce an analgesic having improved safety and efficacy.

It is another object of the present invention to produce a non-opioid analgesic containing reduced amounts of APAP yet providing a desired analgesic effect.

BRIEF DESCRIPTION OF THE FIGURES

FIG. 1 is an isobologram showing the analgesic effect of combinations of APAP and the HCL salt of dimenhydrinate with inhibition of acetylcholine induced writhing in mice.

SUMMARY OF THE INVENTION

Briefly, according to the present invention, there is provided a composition for use as an analgesic comprising:

(a) an analgesic inducing amount of acetaminophen;

(b) from about 1/20 to about 1/500 parts by weight dimenhydrinate or pharmaceutically acceptable salt thereof for each part by weight acetaminophen; and (c) a pharmaceutically acceptable carrier.

There is also provided by the present invention a method for inducing analgesia in mammals comprising administering to the mammal the composition described above.

DETAILED DESCRIPTION OF THE INVENTION

Dimenhydrinate is an anti-emetic, treating motion sickness and nausea, now sold for this use in formulations under a variety of names. It has the chemical formula:

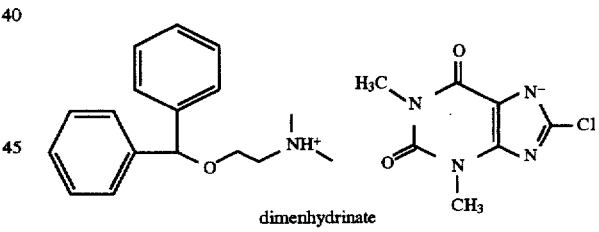

dimenhydrinate

The preparation of dimenhydrinate is well known and a description of a suitable process for its preparation may be found in Cusic, Science 109, 574 (1949) and in U.S. Pat. Nos. 2,499,058 and 2,534,813 (1950 to Searle). In the case of dimenhydrinate, the pharmaceutically acceptable salts referred to above are generally salts with strong mineral acids. Representative of suitable such acids are hydrochloric, hydrobromic, hydroiodic, perchloric, sulfuric, nitric, phosphoric, methanesulfonic or hydroxyethanesulfonic.

To make the combination products of the present invention, the APAP is compounded with the dimenhydrinate in a suitable carrier in the proportions recommended above. Preferrably, there are from about 1/50 to about 1/200 parts by weight dimenhydrinate or pharmaceutically acceptable salt thereof for each part by weight APAP. Most preferrably, there are about 1/100 parts by weight dimenhydrinate or pharmaceutically acceptable salt thereof for each part by weight APAP. In a preferred embodiment of the present invention, the dimenhydrinate is present only to enhance the analgesic effect of the acetaminophen. In such case, the dimenhydrinate should be present in an amount insufficient to produce substantial relief from motion sickness or nausea.

It is well known that APAP is only poorly soluble in water. Thus, for effective administration, it is desirable to employ methods designed to improve the availability of the APAP, such as, grinding the APAP to a small particle size or using a surface active agent to stabilize the suspension and/or act as a solubilizing agent. Suitable such agents include well known surfactants such as glyceryl monooleate, polyoxyethylene sorbitan fatty acid esters, polyvinyl alcohol, sorbitan esters, benzalkonium chloride, benzethonium chloride, cetrimide, docusate sodium and sodium lauryl sulfate. Suitable such agents may also include solubilizing agents/ wetting agents such as polyoxyethylene castor oil derivatives, poloxamer, polyoxyethylene stearates, polyoxyethylene alkylene ethers, stearic acid, lecithin, glyceryl monostearate, cyclodextrins and benzyl benzoate. Suitable such agents may also be emulsifying agents such as acacia, anionic emulsifying wax, carbomer, cetostearyl alcohol, cetyl alcohol, cholesterol, diethanolamine, hydrous lanolin, hydroxypropyl cellulose lanolin, lanolin alcohols, methyl cellulose, mineral oil, monobasic sodium phosphate, monoethanolamine, nonionic emulsifying wax, oleic acid, propylene glycol alginate and triethanolamine. Persons skilled in the art can easily determine how much of such a surface active agent to employ. Generally, there might be used from about 0.05 to about 2.5% by weight of such surface active agent based on the total weight of APAP and dimenhydrinate. Surface active agents are generally described in the HANDBOOK OF PHARMACEUTICAL EXCIPIENTS, 2nd Edition, APhA, 1994.

Compositions of the present invention may be used to treat mild to moderately severe pain in warm-blooded animals such as humans by administration of an analgesically effective dose. The dosage range, based on the principle active ingredient would be from about 10 to 2000 mg, in particular about 25 to 1000 mg or about 100 or 500 mg, of active ingredient 1 to 4 times per day for an average (70 kg) human although it is apparent that activity of individual compounds of the invention will vary as will the pain being treated. Pharmaceutical compositions of the invention comprise the active ingredients as defined above, particularly in admixture with a pharmaceutically-acceptable carrier. For safety, the dose of dimenhydrinate should not exceed about 400 mg per day, for an average (70 kg) human.

The following are more specific examples of embodiments of the present invention:

TABLET 1—500 mg APAP and 5 mg dimenhydrinate in a 600 mg tablet, 1 or 2 tablets to be administered to an average adult every 4 to 6 hours, not to exceed 8 tablets daily.

TABLET 2—325 mg APAP and 16 mg dimenhydrinate in a 400 mg tablet, 1 or 2 tablets to be administered to an average adult every 4 to 6 hours, not to exceed 12 tablets daily.

ELIXIR 1—160 mg APAP and 8 mg dimenhydrinate in 5 mL of liquid excipient, ½ to 3 teaspoons dose to be administered to a child, depending on weight, every 4 to 6 hours, not to exceed 6 doses in 24 hours.

To prepare the pharmaceutical compositions of this invention, the compounds of the invention are intimately admixed with a pharmaceutical carrier according to conventional pharmaceutical compounding techniques, which carrier may take a wide variety of forms depending of the form of preparation desired for administration, e.g., oral or parenteral such as intra muscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. Of course, instead of administering the active ingredients as a single composition, they may be administered simultaneously of sequentially as separate compositions. To obtain the advantages described herein, it is only important that the active ingredients be administered in combination, regardless of whether they are in the same tablet, capsule, powder, injection or elixir.

The following examples illustrate the invention in greater detail, but are not meant to limit its scope. The analytical data for all examples are the experimental values.

EXAMPLES

The combination products of Table I were prepared with active ingredients which were administered in distilled water containing containing one drop of Tween® 80 surface active agent (containing 100% polysorbate 80, a monooleate of polyoxyethylenesorbitan with a fatty acid content of about 75% oleic acid and the balance linoleic, palmitic and stearic acids) per 10 ml of preparation. The concentration of the active ingredients in the distilled water was such to provide a dosing volume of about 10 ml/kg. The activity of the combination products of Table I as analgesic agents may be demonstrated by the mouse acetylcholine-bromide induced constriction assay as described below:

Mouse Acetylcholine Bromide-Induced Abdominal Constriction Assay

The mouse acetylcholine-induced abdominal constiction assay, as described by Collier et al. in Brit. J. Pharmacol. Chem. Ther., 32:295–310, 1968, with minor modifications was used to assess analgesic potency of the combination products herein. The test drugs and appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs).

Between 10 and 15 animals were used in each of the drug treated groups. At least three doses were used to determine each dose response curve and $ED_{50}$ (that dose which would produce 50% analgesia). An experimental design was used which permitted the complete randomization of the separate dosage forms tested. The $ED_{50}$ values and their 95% fiducial limits were determined by a computer assisted probit analysis.

TABLE 1

Mouse Acetylcholine-Bromide Induced Abdominal Constriction Assay
Acetaminophen (APAP) and HCl salt of Dimenhydrinate (DMHD)

| Ratio | Dose (mg/kg, p.o.) APAP | Dose (mg/kg, p.o.) DMHD | # of mice with no writhing | $ED_{50}$ at 30 min (95% con. int.) APAP | $ED_{50}$ at 30 min (95% con. int.) DMHD |
|---|---|---|---|---|---|
| APAP Only | 10 | 0 | 1/15 | 169.5 (91.9–352.2) | 0 |
|  | 30 | 0 | 2/15 |  |  |
|  | 100 | 0 | 5/15 |  |  |
|  | 300 | 0 | 9/15 |  |  |
|  | 1000 | 0 | 13/15 |  |  |
| 100:1 | 3 | 0.03 | 3/15 | 39.7 (18.3–94.8) | 0.4 (0.2–0.9) |
|  | 10 | 0.1 | 4/15 |  |  |
|  | 30 | 0.3 | 6/15 |  |  |
|  | 100 | 1 | 7/15 |  |  |
|  | 300 | 3 | 15/15 |  |  |
| 10:1 | 10 | 1 | 2/15 | 63.3 (36.4–113.6) | 6.3 (3.6–11.4) |
|  | 30 | 3 | 4/15 |  |  |
|  | 100 | 10 | 8/15 |  |  |
|  | 300 | 30 | 14/15 |  |  |
| 1:1 | 3 | 3 | 3/15 | 11.4 (6.9–18.4) | 11.4 (6.9–18.4) |
|  | 10 | 10 | 5/15 |  |  |
|  | 17 | 17 | 8/15 |  |  |
|  | 30 | 30 | 13/14 |  |  |
| 1:10 | 0.3 | 3 | 3/15 | 1.1 (0.6–1.9) | 11 (5.6–19.3) |
|  | 1 | 10 | 7/15 |  |  |
|  | 3 | 30 | 10/14 |  |  |
|  | 10 | 100 | 14/14 |  |  |
| 1:100 | 0.1 | 10 | 3/15 | 0.2 (0.1–0.3) | 19.4 (9.7–31.1) |
|  | 0.2 | 20 | 9/14 |  |  |
|  | 0.3 | 30 | 10/15 |  |  |
|  | 1 | 100 | 12/14 |  |  |
| DMHD Only | 0 | 1 | 2/15 | 0 | 7 (4.2–12.4) |
|  | 0 | 3 | 3/15 |  |  |
|  | 0 | 10 | 7/15 |  |  |
|  | 0 | 30 | 15/15 |  |  |

The results of Table I are plotted in FIG. 1. The diagonal line joining the $ED_{50}$ values of the two drugs given separately represents the expected simple additivity of a composition at different component ratios. The $ED_{50}$ values falling in the area under the line of additivity suggests superadditivity, i.e. unexpected enhancement of effects.

What is claimed is:

1. A composition for use as an analgesic comprising:
   (a) an analgesic inducing amount of acetaminophen;
   (b) from about 1/20 to about 1/500 parts by weight dimenhydrinate or pharmaceutically acceptable salt thereof for each part by weight acetaminophen; and
   (c) a pharmaceutically acceptable carrier.

2. The composition of claim 1 which comprises from about 1/50 to about 1/200 parts by weight dimenhydrinate or pharmaceutically acceptable salt thereof for each part by weight acetaminophen.

3. The composition of claim 1 which comprises about 1/100 parts by weight dimenhydrinate or pharmaceutically acceptable salt thereof for each part by weight acetaminophen.

4. The composition of claim 1 in a dosage form containing 10 to 2000 mg of acetaminophen.

5. The composition of claim 1 in a dosage form containing 25 to 1000 mg of acetaminophen.

6. The composition of claim 1 in a dosage form containing 100 to 500 mg of acetaminophen.

7. The composition of claim 1 in a dosage form containing dimenhydrinate in an amount insufficient to produce substantial relief from motion sickness or nausea.

8. The composition of claim 1 which contains a sufficient amount of surface active agent to stabilize a suspension of the acetaminophen.

9. The composition of claim 8 wherein the surface active agent is selected from the group consisting of glyceryl monooleate, polyoxyethylene sorbitan fatty acid esters, polyvinyl alcohol, sorbitan esters, benzalkonium chloride, benzethonium chloride, cetrimide, docusate sodium, sodium lauryl sulfate, polyoxyethylene castor oil derivatives, poloxamer, polyoxyethylene stearates, polyoxyethylene alkylene ethers, stearic acid, lecithin, glyceryl monostearate, cyclodextrins, benzyl benzoate, acacia, anionic emulsifying wax, carbomer, cetostearyl alcohol, cetyl alcohol, cholesterol, diethanolamine, hydrous lanolin, hydroxypropyl cellulose lanolin, lanolin alcohols, methyl cellulose, mineral oil, monobasic sodium phosphate, monoethanolamine, nonionic emulsifying wax, oleic acid, propylene glycol alginate and triethanolamine.

10. A method for inducing analgisia in a mammal comprising the step of administering a combination comprising:
    (a) an analgesic inducing amount of acetaminophen;
    (b) from about 1/20 to about 1/500 parts by weight dimenhydrinate or pharmaceutically acceptable salt thereof for each part by weight acetaminophen; and
    (c) a pharmaceutically acceptable carrier.

11. The method of claim 10 wherein said combination comprises from about 1/50 to about 1/200 parts by weight dimenhydrinate or pharmaceutically acceptable salt thereof for each part by weight acetaminophen.

12. The method of claim 10 wherein said combination comprises about 1/100 parts by weight dimenhydrinate or pharmaceutically acceptable salt thereof for each part by weight acetaminophen.

13. The method of claim 10 wherein said combination comprises dimenhydrinate in an amount insufficient to produce substantial relief from motion sickness or nausea.

* * * * *